US00PP20372P2

(12) United States Plant Patent
Snoeijer

(10) Patent No.: US PP20,372 P2
(45) Date of Patent: Sep. 29, 2009

(54) ***CLEMATIS* PLANT NAMED 'ZOSTIWA'**

(50) Latin Name: ***Clematis* hybrid**
Varietal Denomination: Zostiwa

(76) Inventor: Wim Snoeijer, Vest 162, 2801 TX Gouda (NL)

( * ) Notice: Subject to any disclaimer, the term of this patent is extended or adjusted under 35 U.S.C. 154(b) by 0 days.

(21) Appl. No.: 12/228,020

(22) Filed: Aug. 8, 2008

(51) Int. Cl.
*A01H 5/00* (2006.01)

(52) U.S. Cl. ..... Plt./228
(58) Field of Classification Search ..... Plt./228
See application file for complete search history.

*Primary Examiner*—June Hwu
(74) *Attorney, Agent, or Firm*—Penny J. Aguirre

(57) ABSTRACT

A new cultivar of hybrid *Clematis*, 'Zostiwa', characterized by its free-flowering habit, its upright facing violet-blue flowers combined with numerous red-purple tipped stamens, its climbing growth habit, and its cold hardiness to U.S.D.A. Zone 6.

3 Drawing Sheets

Botanical classification: *Clematis* hybrid.
Variety denomination: 'Zostiwa'.

BACKGROUND OF THE INVENTION

The present invention relates to a new and distinct cultivar of *Clematis*, botanically of hybrid origin and classified in the Patens Group, and will be referred to hereafter by its cultivar name, 'Zostiwa'. 'Zostiwa' is grown as an herbaceous climber for landscape use and for use as a flowering potplant for the terrace.

'Zostiwa' was selected as unique amongst a group of seedlings that the inventor grew for evaluation in his nursery in Boskoop, The Netherlands. The goal of the selection was to select a hardy climber with uniquely colored flowers that could be grown for different purposes in the garden. 'Zostiwa' was selected by the inventor in summer of 2002 and derived from seeds collected in 1999 and sown in 2000 from open pollinated *Clematis* 'Piilu' (not patented).

Asexual reproduction of the new cultivar was first accomplished by internodial stem cuttings under the direction of the inventor in Boskoop, The Netherlands in 2002. The characteristics of this cultivar have been determined to be stable and are reproduced true to type in successive generations.

SUMMARY OF THE INVENTION

The following traits have been repeatedly observed and represent the characteristics of the new cultivar as grown outdoors for 5 years in Boskoop, The Netherlands. These attributes in combination distinguish 'Zostiwa' from other cultivars of *Clematis* known to the inventor.

1. 'Zostiwa' exhibits upright facing flowers that are violet-blue in color.
2. 'Zostiwa' is free flowering in spring with additional flowering in summer.
3. 'Zostiwa' exhibits flowers with numerous stamens that are white with red-purple tips.
4. 'Zostiwa' exhibits a climbing growth habit.
5. 'Zostiwa' is cold hardy to U.S.D.A. Zone 6.

The new cultivar differs from its parent plant, 'Piilu', primarily in having larger flowers that are violet-blue in color. Close comparisons are *Clematis* 'Ivan Olsson' and 'Miss Bateman' (both unpatented). 'Ivan Olsson' differs from 'Zostiwa' in having flowers that are violet-blue with white centers and in having flowers that fade in color and are not as long lasting. 'Miss Bateman' differs in having flowers that are white, not as long lasting, and rarely present in summer.

BRIEF DESCRIPTION OF THE DRAWING

The accompanying colored photographs illustrate the overall appearance and distinct characteristics of the new *Clematis*. The photographs were taken of a plant of 'Zostiwa' as grown in a trial bed for 3 years in The Netherlands.

The photograph in FIG. 1 shows the flowering habit in spring.

Figure 1:
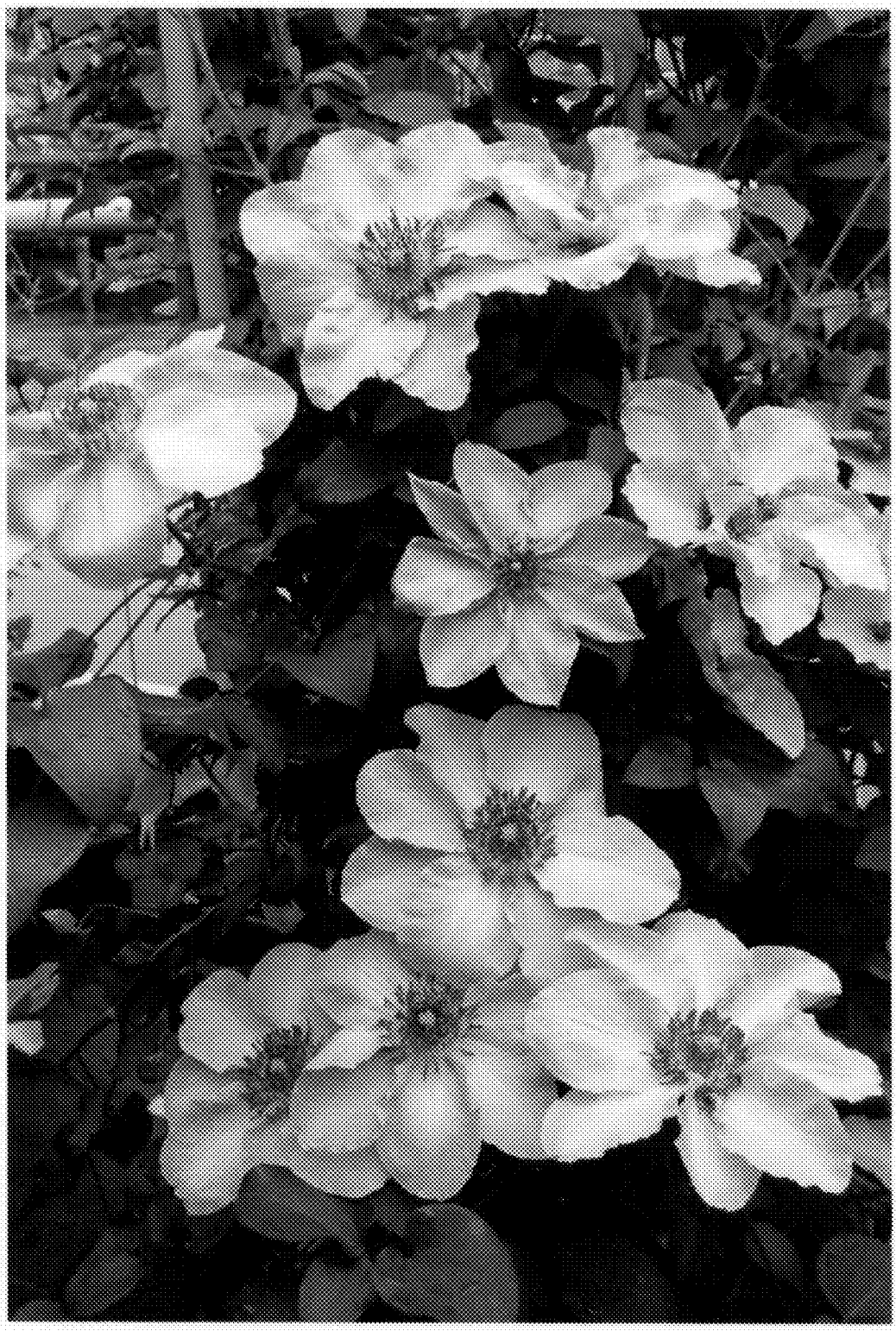
Figure 2:
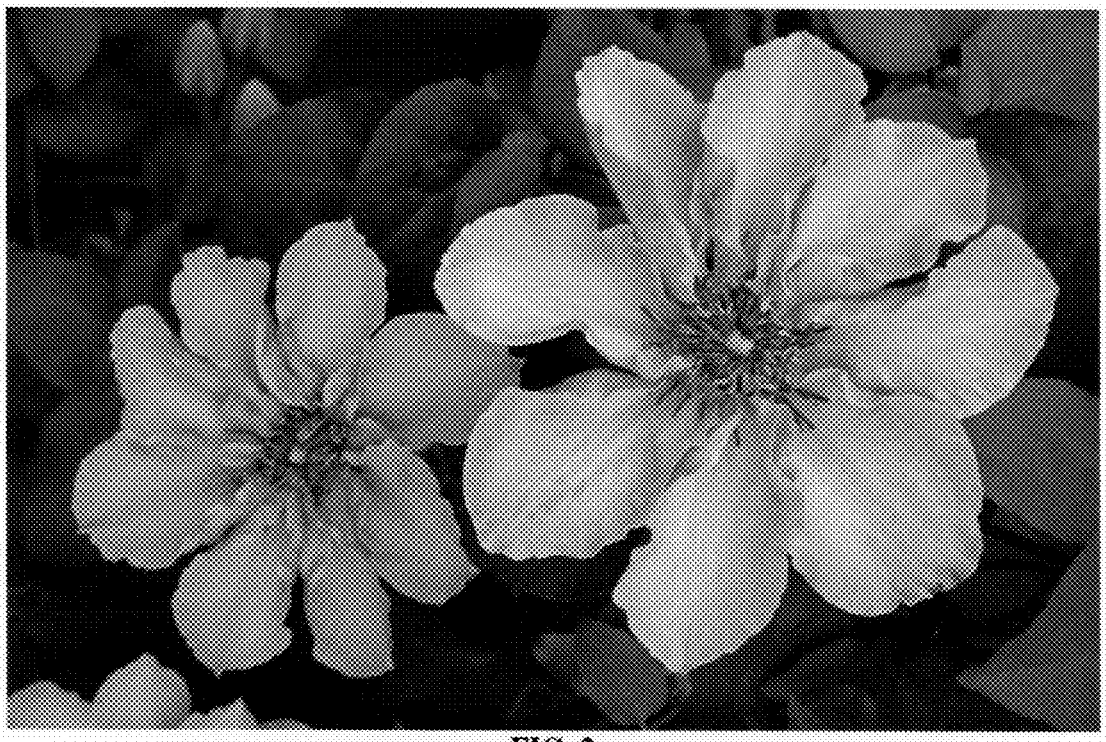

The photograph in FIG. 2 provides a close-up view of a flower in May and

Figure 3:
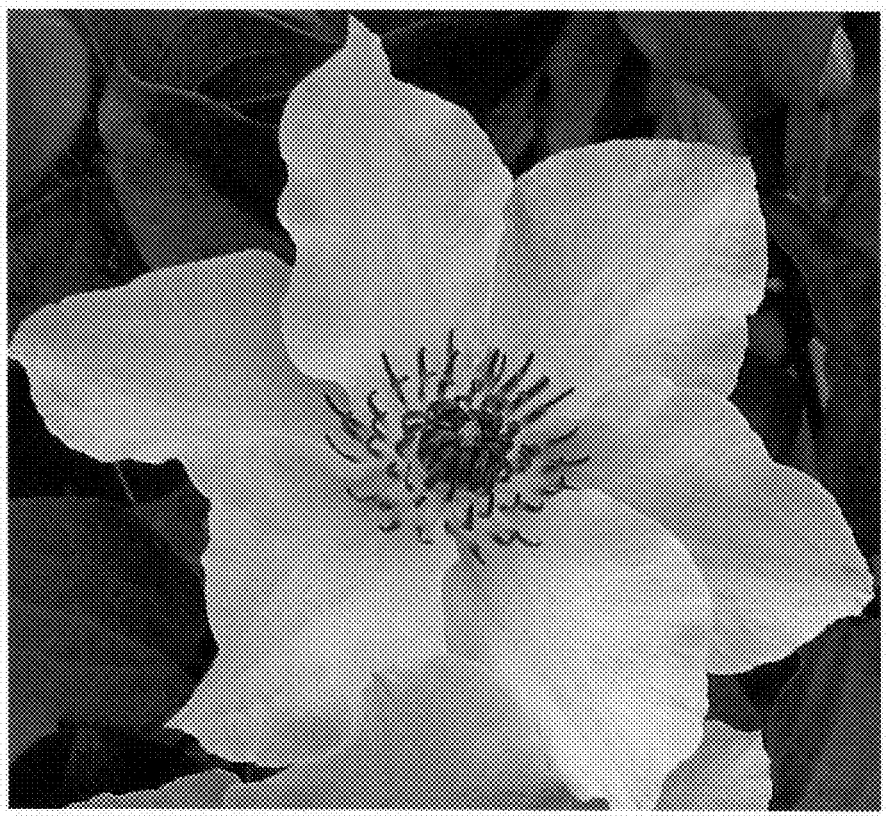

The photograph in FIG. 3 provides a close-up view of a flower in July.

Figure 4:
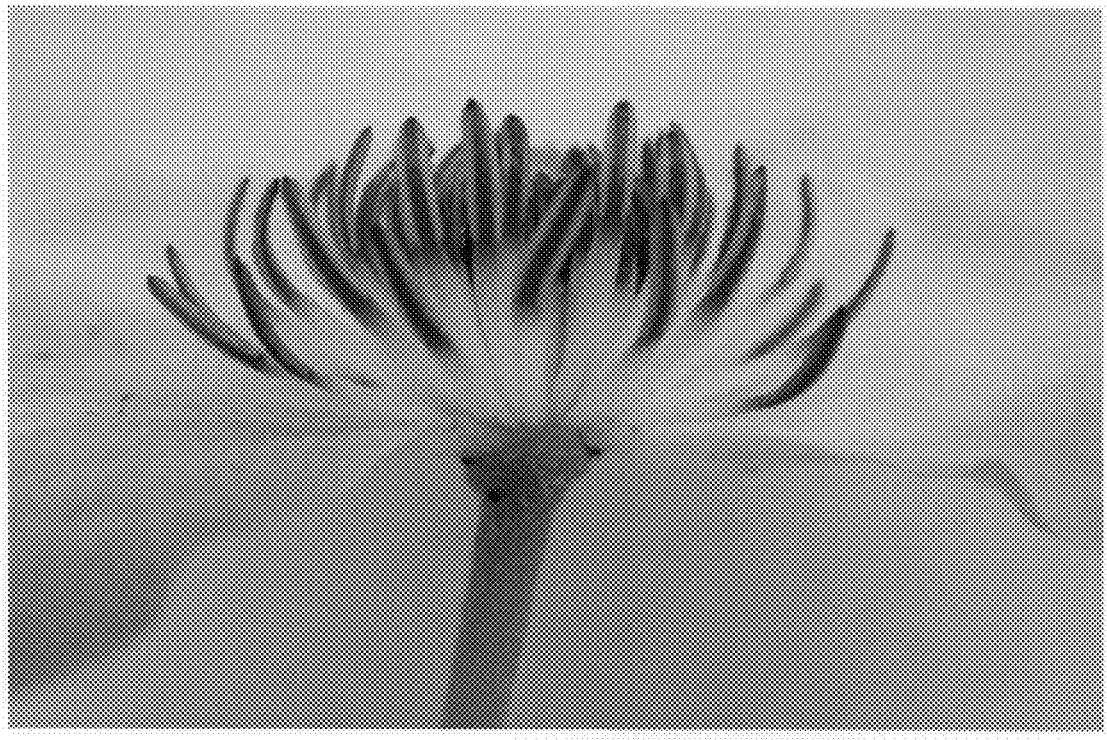
Figure 5:
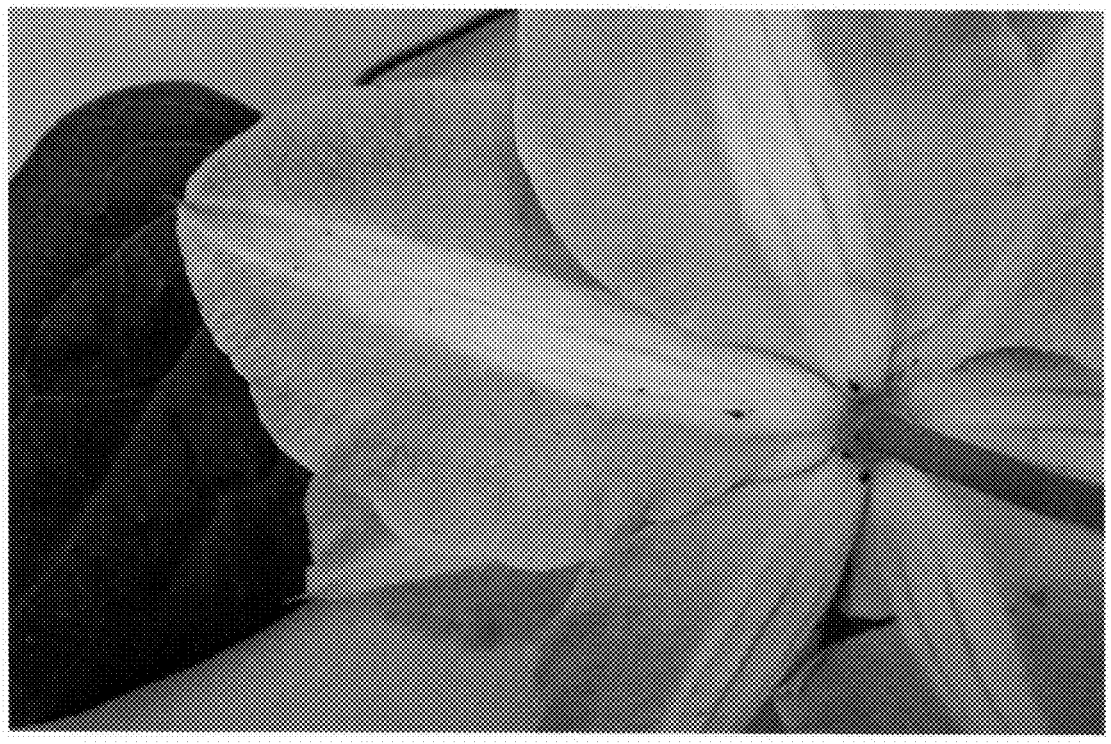

The photograph in FIG. 4 provides a close-up view of the stamens of a flower of 'Zostiwa' in July and The photograph in FIG. 5 provides a close-up view of the back of a flower of 'Zostiwa' in July.

The colors in the photographs are as close as possible with the digital photography techniques available, the color values cited in the detailed botanical description accurately describe the colors of the new *Clematis*.

DETAILED BOTANICAL DESCRIPTION

The following is a detailed description of 3 year-old plants of 'Zostiwa' as grown outdoors in full sun in a test plot in Boskoop, The Netherlands. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Botanical classification.*—'Zostiwa' is classified in the Patens Group of *Clematis*.

*Blooming period.*—Strong bloom for 4 to 6 weeks in spring with good repeat bloom throughout the summer.

*Plant habit.*—Herbaceous climber.

*Height and spread.*—Three year-old plant is about 15 cm at base with a height of about 3 m when lightly pruned after spring flowering.

*Cold hardiness.*—U.S.D.A. Zone 6.

*Culture.*—Moist but well-drained soils in full sun with roots shaded.

*Diseases.*—No particular resistance to diseases has been observed.

*Root description.*—Fleshy.

Growth and propagation:

*Propagation.*—Internodial softwood cuttings from vegetative shoots.

*Root initiation.*—Roots develop in 6 weeks in summer under greenhouse conditions under intermittent mist without supplemental lighting.

*Time required for root development.*—75 to 90 days to develop a 5 cm container from a 5 cm cutting.

*Growth rate.*—Moderately vigorous once planted in the landscape.

Stem description:

*Shape.*—Round and 6 ribbed.

*Stem color.*—Matures quickly to 166A.

*Stem size.*—About 3 m (including peduncle and terminal pedicel) in length, average of 4.5 mm in diameter.

*Stem surface.*—Sparsely covered with fine hairs.

*Internode length.*—Ranges from 4 to 9 cm.

*Branching.*—Basal branching.

Foliage description:

*Leaf arrangement.*—Opposite.

*Leaf division.*—Ternate.

*Leaflet shape.*—Ovate.

*Leaflet base.*—Subcordate.

*Leaflet apex.*—Acuminate.

*Leaflet fragrance.*—None.

*Leaflet venation.*—Primarily reticulate, same as leaf color.

*Leaflet margins.*—Entire.

*Leaflet attachment.*—Petioluled with leaf petioled.

*Leaflet surface.*—Upper and lower surface glabrous with sparse hairs on main veins.

*Leaflet size.*—Up to 7 cm in length and 4 cm in width.

*Leaflet color.*—Upper surface 147A, lower surface 147B.

*Petioles and petiolules.*—1 to 7 cm in length and about 1.5 mm in width, round in shape, 59A in color, curled in aspect, sparsely hairy surface.

Inflorescence description:

*Inflorescence type.*—Solitary.

*Inflorescence arrangement.*—Terminal and axillary on young shoots.

*Peduncles.*—4 to 8 cm in length and an average of 2 mm in width, 143C in color, surface sparsely covered with short hairs, bracts; simple, ovate in shape, about 6 cm in length and 4 cm in width, same color as leaflets, surface sparsely covered with hairs.

*Bud description.*—Ovate in shape, up to 4 cm in length and 2 cm in width, 144B in color with tint of 59A and tepal margins 155A.

*Flower fragrance.*—None.

*Lastingness of flowers.*—Individual flowers last about 7 days, tepals are caducous followed by stamens.

*Flower quantity.*—About 50 flowers on a 3 year-old plant.

*Flower type.*—Single, rotate, round in shape in spring, star-shaped in summer.

*Flower aspect.*—Upright facing.

*Flower size.*—Range from 6 to 10 cm in diameter and about 3 cm in depth.

*Tepal number.*—Typically 8 on spring flowers and 6 on summer flowers.

*Tepal shape.*—Broadly elliptic.

*Tepal apex.*—Acute to obtuse and mucronate.

*Tepal base.*—Cuneate.

*Tepal margins.*—Entire, wavy when first open.

*Tepal surface.*—Upper surface is glabrous, lower surface is glabrous with very short tomentose area towards middle, especially on veins.

*Tepal color.*—Upper surface spring; 91C with tints of N88D and center section suffused with 155C, upper surface summer; 91C with tints of N88D, lower surface spring and summer; 92B with 92A near margin, base and center area 157D with veins 92A.

*Tepal size.*—Up to 5 cm in length and an average of 3.4 cm in width.

Reproductive organs:

Gynoecium.—Numerous pistils (about 50), 1 cm in length, style is 11D with 165D markings in color and plumose, ovary is superior, hairy and143C in color.

*Androcoecium.*—Numerous stamens (about 75), filaments are 3 to 7 mm in length and 1 mm in width, glabrous, and 155A in color with tip 60D near anthers, anthers are 59D in color, connective is 59A in color and obtuse and glabrous, pollen is moderate in quantity and 165D in color.

*Seed.*—Seed data was not available, seed heads are not a distinguishing characteristic.

It is claimed:

1. A new and distinct cultivar of *Clematis* plant named 'Zostiwa' as herein illustrated and described.

* * * * *